United States Patent [19]

Medenica

[11] Patent Number: 5,660,833

[45] Date of Patent: Aug. 26, 1997

[54] ANTI-TUSSIVE COMPOSITION

[76] Inventor: Rajko D. Medenica, 2250 Broadway & 81st, Apt. 7A, New York, N.Y. 10024

[21] Appl. No.: 658,744

[22] Filed: Jun. 5, 1996

[51] Int. Cl.$^6$ .......................... A61K 35/78; A61K 33/14; A61K 31/135
[52] U.S. Cl. ...................... 424/195.1; 424/664; 514/653
[58] Field of Search ................................. 424/195.1, 664; 514/653

[56] References Cited

U.S. PATENT DOCUMENTS

| | | |
|---|---|---|
| 3,789,125 | 1/1974 | Kuger et al. . |
| 3,958,002 | 5/1976 | Stenger et al. . |
| 4,489,062 | 12/1984 | Lowe et al. . |
| 4,552,962 | 11/1985 | Brossi . |

OTHER PUBLICATIONS

Martindale, The Extra Pharmacopoeia, 28th ed., published by The Pharmaceutical Press (London), pp. 671, 686, 687, 691 and 692 1982.

Handbook of Nonprescription Drugs, 8th ed. published by American Pharmaceutical Association (D.C.), pp. 153–161 1986.

IMS World Product Launches Abstract No. 01450226 1973.

*Primary Examiner*—Raymond Henley, III
*Attorney, Agent, or Firm*—DeWitt Ross & Stevens SC

[57] ABSTRACT

An anti-tussive composition comprising essence of anise, senega dry extract, and pure licorice root extract, in combination with a pharmaceutically-suitable liquid carrier, and a method of treating cough in humans, is disclosed.

17 Claims, No Drawings

ANTI-TUSSIVE COMPOSITION

FIELD OF THE INVENTION

The invention is directed to an anti-tussive containing natural plant extracts which is non-addictive and effectively suppresses coughing due to various etiologies.

DESCRIPTION OF THE PRIOR ART

The cough mechanism is an explosive expiration which provides a means for clearing the tracheal and bronchial trees of accumulated secretions and/or foreign bodies. Coughing is among the most frequently reported cardio-respiratory symptoms and perhaps the most common symptom for which medical attention is sought. The cough mechanism is initiated by an appropriate stimulus which elicits a deep inspiration. Physiologically, this is followed by closure of the epiglottis and relaxation of the diaphragm. A sharp muscle contraction against the closed epiglottis then follows. This produces a greatly increased intra-thoracic and intra-airway pressure. The positive intra-thoracic pressure causes a narrowing of the trachea due to enfolding of its compliant posterior membrane. At this point, the epiglottis opens.

When the epiglottis opens, the combination of the large pressure differential between the thoracic cavity and the atmosphere, coupled with the narrowing of the trachea, produces a massively increased rate of air flow through the trachea. In fact, at the instant the epiglottis opens, the air flow rate through the trachea momentarily approaches the speed of sound. The shearing force created by this massively increased flow rate is normally effective to expectorate mucus and foreign materials from the airway. Thickening of mucosal secretions or physical blockage of the epiglottis (as when an endo-tracheal tube is present), however, greatly decreases the effectiveness of the coughing mechanism.

Coughing is caused by an extremely wide range of different factors. For instance, coughing is produced by inflammatory mechanisms, mechanical disorders, and chemical and thermal stimulation of the cough receptors. For instance, inflammatory stimuli can be initiated by edema of the mucosal membranes. The edema, in turn, can be from any etiology, such as bacterial or viral infection, the common cold, or excessive cigarette smoking. Inflammatory stimuli may also be elicited by irritation from exudative processes such as post-nasal drip and gastric reflux. Such stimuli may arise in the airways, as in laryngitis, bronchitis, and the like, or in the lungs proper, as in the case of pneumonia or an abscess in the lungs.

Mechanical stimuli giving rise to coughing are caused by inhalation of particulate matter. Other mechanical disorders which result in compression of the air passages or increased pressure upon any area of the respiratory system may result in coughing. Such mechanical difficulties may arise from intra-mural or extra-mural etiologies. For instance, extra-mural causes of coughing include extra-mural pressure caused by an aortic aneurysm, granulomas, pulmonary neoplasms, mediastinal tumors, and the like. Intra-mural lesions, such as bronchiogenic carcinoma, bronchial adenoma, the presence of foreign bodies or bronchial asthma also result in coughing. Decreased pliancy of the respiratory membranes may also result in chronic coughing, as in the case of patients suffering from cystic fibrosis.

Chemical stimuli, such as the inhalation in irritant gases such as cigarette smoke or chemical fumes, may also elicit coughing. Other chemical entities result in coughing due to their reactive effect upon the respiratory system itself or on the balance and uptake of respiratory gases. Additionally, many chemical agents induce coughing due to their reaction with enzymes involved in the respiratory process.

Lastly, thermal stimuli, such as the inhalation of either very hot or cold air, may also result in coughing.

In several disease states in humans, a persistent cough is often the sole presenting symptom. For instance, patients suffering from bronchial asthma often seek medical treatment only after being unable to rid themselves of incessant coughing.

In some medical conditions, most notably, asthma, the cough mechanism itself may further aggravate the patient's condition. Asthma is a condition marked by recurrent attacks of paroxysmal dyspnea with wheezing, which is due to spasmatic contraction of the bronchi. The condition is caused by various etiologies: some cases of asthma are allergic manifestations in sensitized persons, while others are provoked by a variety of factors including vigorous exercise, chemical or particulate irritation, or even psychological stress. The violent contractions of the thoracic cavity which accompany coughing further aggravates already irritated respiratory membranes.

Due to the prevalence of coughing, a large number of anti-tussive formulations have been reported in the patent literature. For instance, Kuger et al., U.S. Pat. No. 3,789,125, describe an anti-tussive medicament containing a halo-substituted, 2-amino-benzylamine-amid as an active ingredient.

Stenger et al., U.S. Pat. No. 3,958,002, describe an anti-tussive medicament which contains ortho-cresotamide derivatives. Lowe et al., U.S. Pat. No. 4,489,062, describe an anti-tussive pharmaceutical composition in which the active ingredient is a polypeptide derivative. Brossi, U.S. Pat. No. 4,552,962, describes anti-tussive compositions containing morphine-like dextrorotary 6-keto morphinan. The compounds described by Brossi are the non-natural enantiomers of naturally-occurring levorotary species.

As evidenced by the above-noted references, the cough mechanism in humans has been treated with a remarkably broad range of chemical therapeutic agents. The above-noted patents are a small sampling of the large number of anti-tussive compositions described in the prior art. However, none of the prior art known to the inventor describes or renders obvious the anti-tussive composition disclosed or claimed herein.

SUMMARY OF THE INVENTION

The present invention is directed to an anti-tussive composition which comprises essence of anise, senega dry extract, and pure licorice root extract, in combination with a pharmaceutically-suitable liquid carrier.

The invention is further drawn to an anti-tussive composition which comprises from 10 to 50 mg/ml ammonium chloride, from 0.5 to 1.0 mg/ml essence of anise, from 1.0 to 3.0 mg/ml senega dry extract, and 20.0 to 80.0 mg/ml pure licorice root extract, in combination with a pharmaceutically-suitable liquid carrier.

The invention is also directed to a method of suppressing cough in humans. The method comprises administering an effective cough-suppressant amount of an anti-tussive composition containing essence of anise, senega dry extract, and pure licorice root extract, in combination with a pharmaceutically-suitable liquid carrier, to a human subject in need thereof.

The method described above is further drawn to a method of suppressing cough in humans which comprises administering an effective cough-suppressant amount of an anti-tussive composition containing from 10 to 50 mg/ml ammonium chloride, from 0.5 to 1.0 mg/ml essence of anise, from 1.0 to 3.0 mg/ml senega dry extract, and 20.0 to 80.0 mg/ml pure licorice root extract; in combination with a pharmaceutically-suitable liquid carrier, to a human subject in need thereof.

In light of the above discussion, it is a principle aim of the present invention to provide a non-addictive anti-tussive composition which suppresses cough.

It is a further aim of the present invention to provide an anti-tussive medicament containing essence of anise, senega dry extract, and licorice root extract. The medicament may be formulated with or without additional ancillary ingredients such as preservatives, decongestants, bacteriostats, and the like.

The present anti-tussive composition is particularly advantageous in that it quickly and effectively suppresses coughing. It is also very safe because it does not contain narcotics or opiate derivatives which may be habit-forming. The anti-tussive composition is also relatively easy to formulate because it does not require the use of optically active chemical species. Additionally, the anti-tussive composition has a pleasant taste and aroma, and has good organoleptic qualities. This makes the composition ideal for treating children.

These and other aims, objects, and advantages of the anti-tussive medicament disclosed and claimed herein will become clear upon a complete reading of the Detailed Description and claims, below.

DETAILED DESCRIPTION OF THE INVENTION

The anti-tussive composition of the present invention contains three core ingredients, all of which are isolated from natural ingredients. These ingredients are: essence of anise, senega dry extract, and pure licorice root extract. Essence of anise is a volatile oil extracted from *Pimpinella anisum*. Senega dry extract is a concentrated preparation from the dried root of *Polygaia senegal*, a plant of North America which is commonly known as seneca, senega, or snake root. The main constituent of the dried root extract is polygalic acid and senegin. Senega dry extract has been used in veterinary medicine as an expectorant.

Pure licorice root extract is a preparation made from the dried rhizome and roots of a variety of *Glycyrrhiza glabra*. In combination, these three extracts exhibit a synergistic anti-tussive effect in humans.

The extracts per se are known and are commercially available. For instance, anise extract is available from Penta Manufacturing Company (Fairfield, N.J.) and Centercham Inc. CCI (Stamford, Conn.). Licorice root extract is also supplied by Centerchain as well Alfa Chain (Central Islip, N.Y.). Senega dry extract can be purchased from the Meer Corporation (North Bergan, N.J.) and Doctor Madis Laboratories, Inc. (Hackensack, N.Y.).

In addition to the three natural extracts described immediately above, the anti-tussive composition is dissolved within a pharmaceutically-suitable liquid carrier. Suitable liquid carriers include any number of well-known aqueous carriers and ethanolic carriers.

Additionally, the anti-tussive composition may contain sweeteners such as saccharose and preservatives such as methyl-para-hydroxybenzoate. The preferred formulation of the anti-tussive composition also contains ammonium chloride. Ammonium chloride is a systemic and urinary tract acidifying agent and diuretic. The presence of ammonium chloride increases the synergistic anti-tussive effect of the other active ingredients.

Preferably, the anti-tussive contains the following ingredients: ammonium chloride, essence of anise, senega dry extract, pure licorice root extract, ethanol, saccharose, and methyl-para-hydroxybenzoate.

More preferably still, the anti-tussive contains:

from 10 to 50 mg/ml ammonium chloride;

from 0.5 to 1.0 mg/ml essence of anise;

from 1.0 to 3.0 mg/ml senega dry extract;

20.0 to 80.0 mg/ml pure licorice root extract; and from 5 to 20 mg/ml ethanol.

An illustrative embodiment of the anti-tussive composition contains the following ingredients in the amounts noted. The amounts are dissolved within a pharmaceutically-suitable liquid carrier.

ammonium chloride—25 mg/ml;

essence of anise—0.8 mg/ml;

senega dry extract—1.5 mg·ml;

pure licorice root extract—40 mg/ml;

ethanol—12 mg/ml;

saccharose—107 mg/ml; and methyl-para-hydroxybenzoate—1 mg/ml.

Ammonium chloride, ethanol, saccharose and methyl-p-hydroxybenzoate are widely available commercially. For instance, all can be purchased in bulk quantities from the Aldrich Chemical Company (Milwaukee, Wis.), and many other international companies.

The anti-tussive is preferably administered orally. An exemplary dosage in humans is 5 ml orally, four times a day until the symptom subside.

The anti-tussive may also contain a pharmaceutically-suitable topical antibiotic which is suitable for oral administration in humans. A wide range of such antibiotics are well known to those skilled in the art.

EXAMPLES

The following Examples are for illustrative purposes only, to provide a more complete understanding of the present invention. The Examples do not limit the invention disclosed and claimed herein in any fashion.

Example 1

In this study, the above-noted illustrative formulation was blind-administered to 314 patients presenting at a European clinic with various diagnoses in addition to cough. The average age of the patient sample was 48 years old; the youngest patient treated was three years old, and the oldest 102 years old.

The patients were given a dosage of 5 ml of the preferred formulation, per os, four times a day. In a majority of the patients treated in this fashion, coughing subsided within 24 to 48 hours.

The breakdown of the presenting symptoms of the patients treated in this Example was as follows:

| Name of the Disease | No. of Patients | Average Onset of Disappearance of Coughing |
| --- | --- | --- |
| Common Cold | 72 | 3 Days |
| Nocturnal Coughing | 11 | 2 Days |
| Respiratory Infection | 48 | 5 Days |
| Psittacosis | 8 | 4 Days |
| Pulmonary Edema | 14 | 2 Days |
| Smoking Cough | 39 | 2 Days |
| Pulmonary Neoplasms | 25 | 3 Days |
| Viral Pneumopathic | 28 | 6 Days |
| Pulmonary Thromboembolism | 9 | 3 Days |
| Pulmonary Vasculitis (Wegener's Granulomatosis; Good Pasteur's Syndrome; Connective Tissue Disorder) | 12 | 3 Days |
| Hemorrhagic Diathesis including anticoagulant therapy | 8 | 3 Days |
| Tuberculosis | 14 | 4 Days |
| Unknown Etiology | 26 | 5 Days |

The success of the treatment allowed it to be discontinued within 5 days in those patients presenting with the common cold, pulmonary edema, and hemorrhagic diathesis including anticoagulant therapy.

For those patient presenting with nocturnal coughing, respiratory infection, psittacosis, viral pneumopathic symptoms, pulmonary thromboembolism, and coughing of unknown etiology, the composition successfully suppressed coughing after approximately 10 days of treatment.

There are several diseases/conditions in which treatment with the present composition suppresses cough for a temporary span of time, after which, the coughing returns and the treatment must be resumed. Particularly notable in this area are smoker's cough, pulmonary neoplasms, pulmonary vasculitis, and tuberculosis.

Clinical evaluation, laboratory tests, and radiological imaging were performed on each patient during the course of their treatment. This was performed to follow both the evolution of the various disease states of the patients, as well as to detect any adverse reactions to the anti-tussive medication. No toxicity or allergic reactions of any sort were observed during the study. It therefore appears from this study that the anti-tussive medication is well tolerated by a wide range of patients.

This Example shows that the present anti-tussive formulation is an effective medication against cough. The medication is well tolerated and produced a rapid inhibition of coughing without any discernible side effects. In patients presenting with chronic diseases, coughing is temporarily suppressed, but reappears after a time.

Example 2

This Example was performed in identical fashion to Example 1, except that the following formulation was administered:

Ammonium chloride, 25 mg/ml
Essence of Anise, 0.8 mg per ml
Senega dry extract, 1.5 mg/ml
Pure licorice root extract, 40 mg/ml
Ethanol, 12 mg/ml
Saccharose, 107 mg/ml
Methyl-para-hydroxybenzoate, 1 mg per ml
Pseudoephedrine-para-hydrochloride, 4 mg/ml
Phenylephrine-para-hydrochloride, 1 mg/ml
Cetylpyridinium chloride, 0.2 mg/ml Pseudoephedrine-para-hydrochloride is a stereoisomer of ephedrine having less pressor action and central stimulant effect than ephedrine. It is conventionally used in the form of its hydrochloride or sulfate salt. The hydrochloride salt is a known nasal decongestant and bronchial dilator when administered orally It functions to decongest the nasal mucosa in patients suffering allergies, and to relax bronchiole muscles in bronchial asthmatics.

Phenylephrine-para-hydrochloride is a direct-acting sympathomimetic amine that stimulates alpha adrenergic receptors and is a powerful vasoconstrictor. Phenylephrine-para-hydrochloride is a known topical nasal decongestant. It is also administered orally as a component of combination antihistaminic-decongestant preparations.

Cetylpyridinium chloride is a cationic disinfectant used as a topical anti-infective, and can be administered sublingually. It can also be applied topically to intact skin and mucous membranes and also finds use as a preservative in pharmaceutical preparations.

In this study, the above-noted formulation was blind-administered to 247 patients presenting at a European clinic with various diagnoses in addition to cough. The average age of the patient sample was 48 years old; the youngest patient treated was 11 years old, and the oldest 92 years old. There were 182 females and 65 males. The patients in this study presented with the following diagnoses:

| DISEASE | NO. OF PATIENTS |
| --- | --- |
| Influenza Allergic Upper Respiratory Syndrome | 136 |
| Allergic Asthma | 31 |
| Hypersensitivity Eosinophilic Pneumonia | 16 |
| Hay Fever Coughing | 46 |
| Other Allergic Manifestations with Coughing of Unknown Origins | 18 |

As in Example 1, the patients were given 5 ml doses, four times a day. The average number of days until the coughing subsided are tabulated as follows:

| NAME OF THE DISEASE | NO. OF PATIENTS | DISAPPEARANCE OF COUGH |
| --- | --- | --- |
| Influenza Allergic Upper Respiratory Syndrome | 136 | 3 Days |
| Allergic Asthma | 31 | 4 Days |
| Hypersensitivity Eosinophilic Pneumonia | 16 | 7 Days |
| Hay Fever Coughing | 46 | 2 Days |
| Other Allergic Manifestations with Coughing of Unknown Origins | 18 | 8 Days |

As noted above, in some chronic diseases/conditions, it was necessary to repeat the therapy several times. However, during each cycle of treatment, complete inhibition of coughing was obtained.

As in Example 1, clinical evaluation, laboratory tests, and radiological imaging were performed on each patient during the course of their treatment. No generalized or localized side effects were observed.

It is understood that the anti-tussive composition of the present invention is not confined to the particular ingredients and ratios illustrated and described above, but embraces all such modified forms thereof as come within the scope of the following claims.

What is claimed is:

1. An anti-tussive composition comprising: ammonium chloride, essence of anise, senega dry extract, and pure licorice root extract, in combination with a pharmaceutically-suitable liquid carrier.

2. The anti-tussive composition according to claim 1, further comprising a nasal decongestant.

3. The anti-tussive composition according to claim 1, further comprising pseudoephedrine-para-hydrochloride.

4. The anti-tussive composition according to claim 1, further comprising phenylephrine-para-hydrochloride.

5. The anti-tussive composition according to claim 1, further comprising cetylpyridinium chloride.

6. The anti-tussive composition according to claim 1, further comprising a pharmaceutically-suitable topical antibiotic suitable for oral administration in humans.

7. The anti-tussive composition according to claim 1, further comprising ethanol.

8. An anti-tussive composition comprising:
   from 10 to 50 mg/ml ammonium chloride;
   from 0.5 to 1.0 mg/ml essence of anise;
   from 1.0 to 3.0 mg/ml senega dry extract; and
   20.0 to 80.0 mg/ml pure licorice root extract;
   in combination with a pharmaceutically-suitable liquid carrier.

9. The anti-tussive composition according to claim 8, further comprising methyl-para-hydroxybenzoate.

10. The anti-tussive composition according to claim 8, further comprising from 5 to 20 mg/ml ethanol.

11. A method of suppressing cough in humans comprising administering an effective cough-suppressant amount of an anti-tussive composition containing ammonium chloride, essence of anise, senega dry extract, and pure licorice root extract, in combination with a pharmaceutically-suitable liquid carrier, to a human subject in need thereof.

12. The method according to claim 11, wherein the anti-tussive composition administered to the human subject in need thereof further comprises a nasal decongestant.

13. The method according to claim 12, wherein the nasal decongestant is pseudoephedrine-para-hydrochloride.

14. The method according to claim 12, wherein the nasal decongestant is phenylephrine-para-hydrochloride.

15. The method according to claim 12, wherein the anti-tussive composition administered to the human subject in need thereof further comprises cetylpyridinium chloride.

16. The method according to claim 12, wherein the anti-tussive composition administered to the human subject in need thereof further comprises ethanol.

17. A method of suppressing cough in humans comprising administering an effective cough-suppressant amount of an anti-tussive composition containing:
   from 10 to 50 mg/ml ammonium chloride;
   from 0.5 to 1.0 mg/ml essence of anise;
   from 1.0 to 3.0 mg/ml senega dry extract; and
   20.0 to 80.0 mg/ml pure licorice root extract;
   in combination with a pharmaceutically-suitable liquid carrier;
to a human subject in need thereof.

* * * * *